United States Patent [19]

Bin

[11] Patent Number: 4,955,869
[45] Date of Patent: Sep. 11, 1990

[54] DISPOSABLE SAFETY SYRINGE WITH A HYPODERMIC NEEDLE

[75] Inventor: Valter Bin, Bruino, Italy
[73] Assignee: Vabin International S.r.L., Cuneo, Italy
[21] Appl. No.: 305,925
[22] Filed: Feb. 3, 1989
[30] Foreign Application Priority Data Feb. 4, 1988 [IT] Italy ............................. 67077 A/88

[51] Int. Cl.⁵ ............................................. A61M 5/32
[52] U.S. Cl. ...................................... 604/195; 604/110
[58] Field of Search ............... 604/195, 192, 187, 196, 604/194, 110, 198

[56] References Cited

U.S. PATENT DOCUMENTS

| | | |
|---|---|---|
| 1,771,219 | 7/1930 | Hein. |
| 4,507,117 | 3/1985 | Vining et al. ........................ 604/196 |
| 4,664,654 | 5/1987 | Strauss. |
| 4,702,738 | 10/1987 | Spencer ............................... 604/198 |
| 4,767,413 | 8/1988 | Haber et al. ......................... 604/198 |
| 4,790,822 | 12/1988 | Haining .............................. 604/195 |
| 4,804,370 | 2/1989 | Haber et al. ......................... 604/195 |

Primary Examiner—John D. Yasko
Attorney, Agent, or Firm—Venable, Baetjer and Howard

[57] ABSTRACT

A disposable safety syringe with a hypodermic needle of a type comprising a syringe body inside which a plunger is guided for sliding movement and wherein said needle is guided for movement to an away position inside the syringe body, further comprises:
- an engagement peg formed at the plunger end integrally therewith;
- a holding pad for said needle arranged to be movable within said body and provided with a seat for engagement with the peg; and
- an elastically yielding seal having a non-uniform thickness and being attached to the plunger end. The needle, as caught up after injection by the plunger peg engaging in a corresponding seat on the pad, is fully retracted into the syringe body and subjected to a sideways push from the seal effective to offset it and make re-use of the syringe impossible.

7 Claims, 3 Drawing Sheets

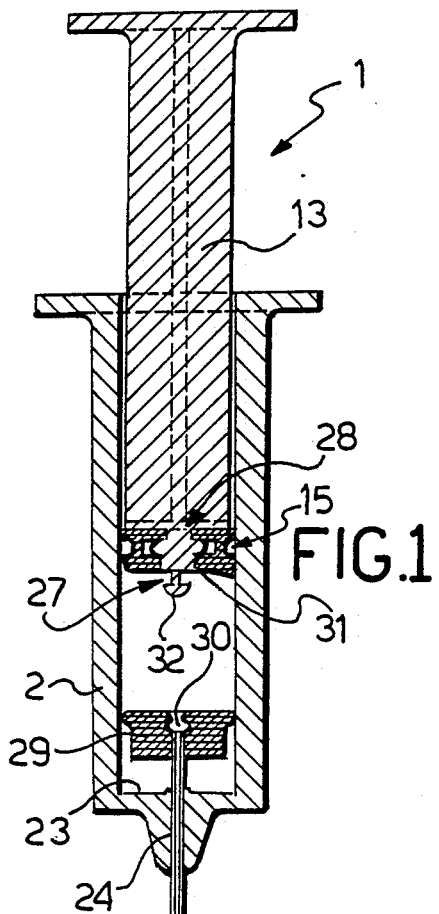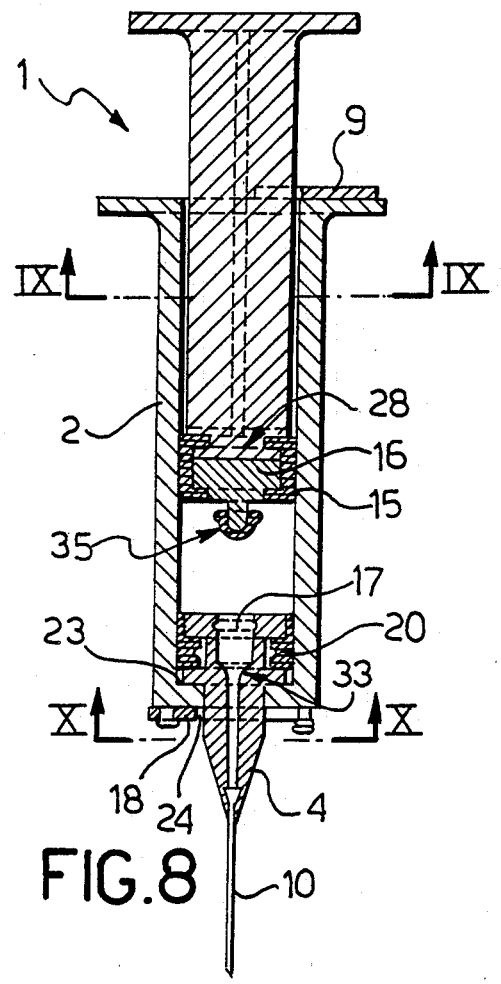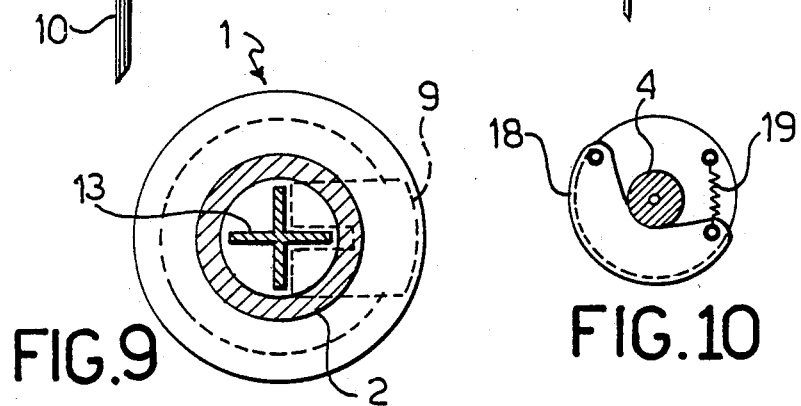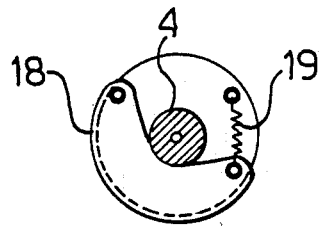

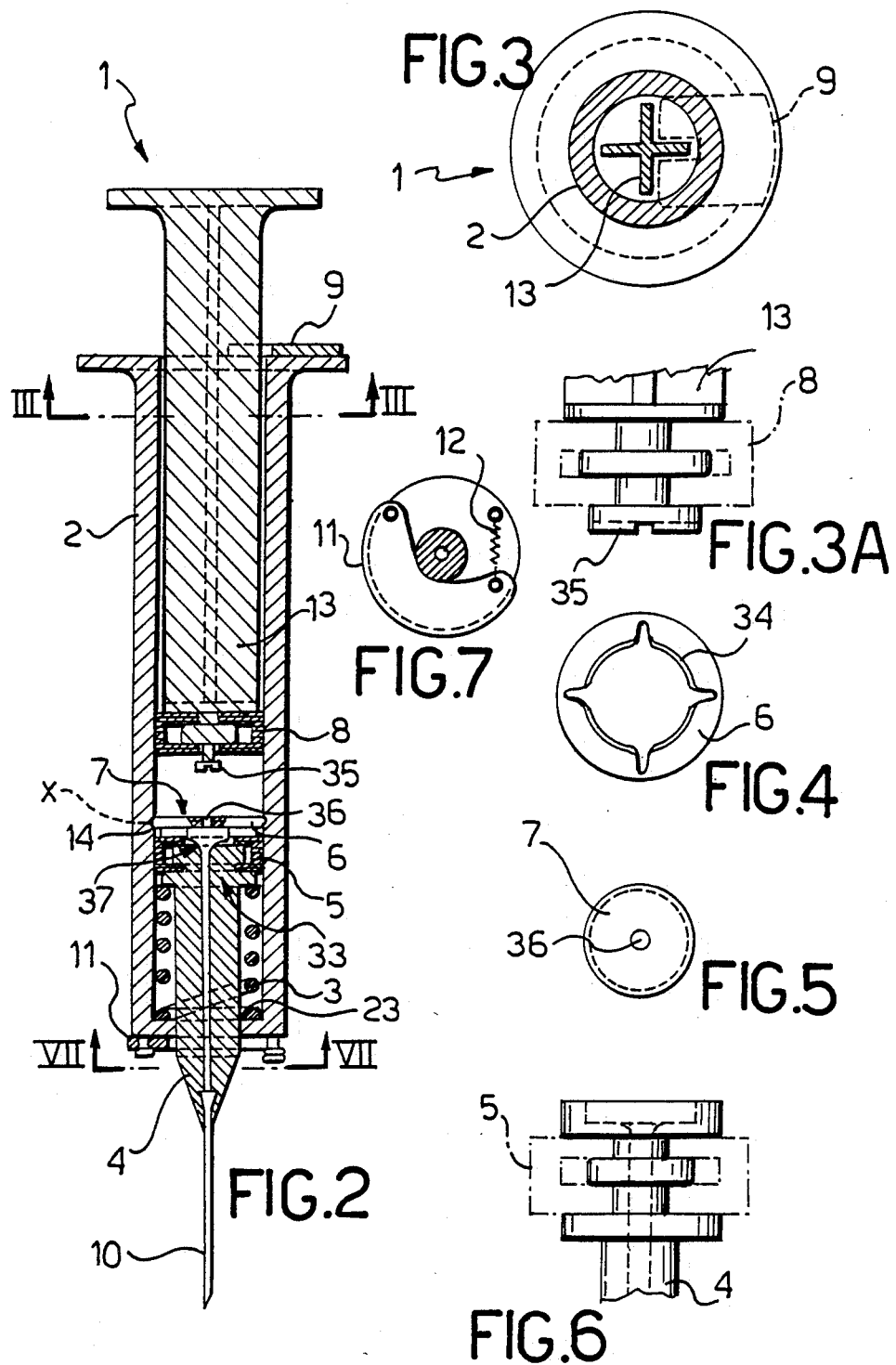

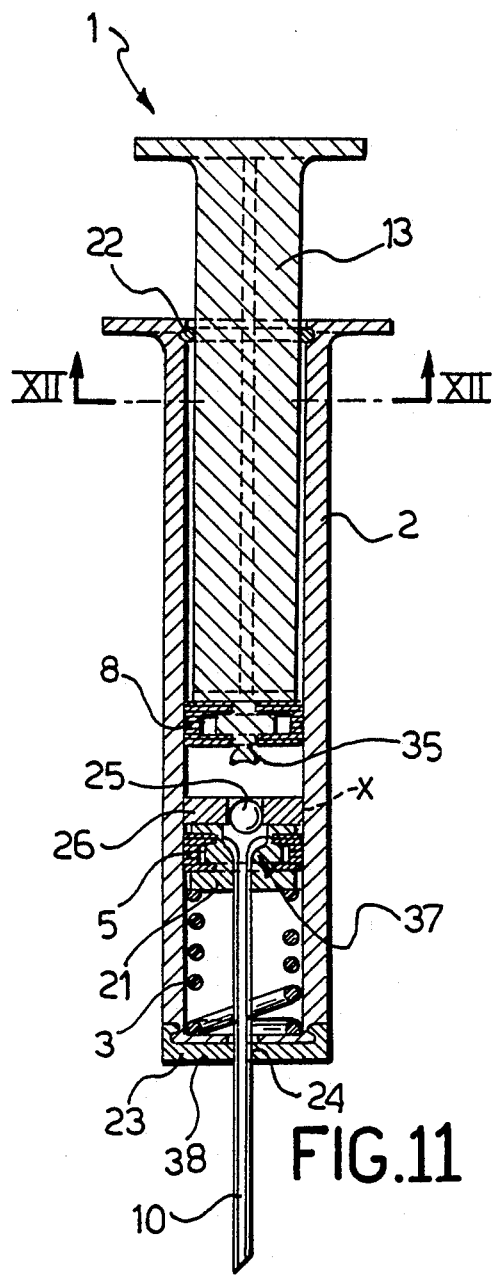
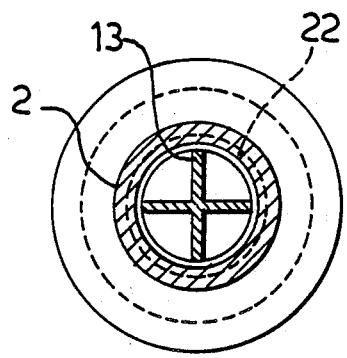
FIG.12
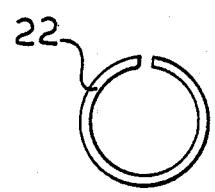
FIG.13
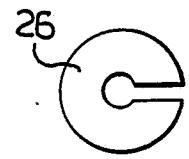
FIG.14
FIG.11

DISPOSABLE SAFETY SYRINGE WITH A HYPODERMIC NEEDLE

DESCRIPTION

This invention relates to a disposable safety syringe with a hypodermic needle, of a type which comprises a syringe body inside which a plunger is guided for sliding movement, said needle being guided for movement to an away position within the syringe body.

It is a well-known fact that disposable syringes of the above type are usually formed from a non-toxic synthetic plastics material, and comprise:

- a tubular syringe body having a conically tapering end into a tip defining a small diameter bore;
- a hypodermic needle having its remote end from its needle point end fitted over said conical end of the syringe body;
- a plunger consisting of a rod fitted removably into the syringe body and being guided within that body for sliding movement therethrough;
- a rubber seal attached to the plunger end fitted into the syringe body and having a slightly larger outside diameter than the inside diameter of that body to provide a tight fit for the plunger; and
- a protective cap for the hypodermic needle.

These five elements constitute the basic components of any disposable syringes currently available on the market, each syringe being merchandised in a respective sealed package on which the manufacturer merely shows a warning to the effect that the syringe is to be used once.

It is a known fact, however, that such syringes are usually left after use mostly anywhere, especially by drug addicts, thereby endangering the health of the community, and children's especially, being carriers of such infections as hepatitis or AIDS.

To prevent such a potential danger, the prior art has proposed the use of a particular syringe type, as described in U.S. Pat. No. 4,702,738.

That patent discloses a syringe comprising a tubular case fitting slidably over the exterior of the syringe body to cover the needle for protection before and after use.

The syringe body is formed with guide flutes for that case, and has toothed means of engagement to lock the case in a position where it would cover the needle.

This prior approach has, first and foremost, the drawback that an additional part is required in the syringe construction, which affects production cost adversely. Furthermore, the case makes for a less easily handled syringe in use, while the provision of the flutes and locking means on the syringe body adds, in turn, to the production costs.

A second prior approach is described instead in U.S. Pat. No. 4,507,117, which discloses a syringe wherein the needle is mounted to a slider movable axially through the interior of the syringe body and equipped with hooking means for engagement with the body bottom to provide a working setting with the needle extended from the body.

The syringe plunger is in turn provided with hooking means whereby the needle slider can be engaged and, on completion of an injection cycle, withdrawn into the syringe body.

The hooking means are releasable catches of the bayonet type which require for their operation rotational movements of both the plunger and the needle-holding slider.

This second approach has, however, a serious drawback in that the needle and its holding slider are normally housed within the syringe body, and requires to be preliminarly pushed into the working position by means of the plunger which, after the slider is anchored on the bottom wall of the syringe body, must be released and driven backwards into its working position.

This, additionally to creating problems during the syringe assembling stage and in the use thereof, impairs the disposable feature of the syringe because the needle, although retractable, may be pushed once again to its working position.

A further prior art approach is described in U.S. Pat. No. 4,767,413, which discloses a syringe for dental use including means for automatically retracting the needle into the syringe body. However, this prior syringe has so many component parts as to be an unduly complicated construction unsuitable for the very large volume manufacturing methods employed with syringes of the disposable type.

Further, not even the latter syringe design can prevent re-use.

The problem underlying this invention is to provide a novel type of disposable safety syringe which has constructional and performance characteristics of great simplicity, such that once it has been used and its needle retracted into the syringe body, there is no way of re-using the same syringe twice, thereby overcoming the noted drawbacks with which the prior art is beset.

This problem is solved by a syringe of the type specified above comprising:

- an engagement peg formed at the plunger end integrally therewith;
- a supporting pad for said needle arranged to be movable axially within said body, in said pad there being formed an engagement seat for said peg; and
- an elastically yielding seal mounted to the plunger end to apply an elastic pressure offset from the needle axis and tending to bring the needle out of alignment once the needle has been retracted into said body.

The features and advantages of the syringe according to the invention will become apparent from the following detailed description of an embodiment thereof, to be taken by way of example and not of limitation in conjunction with the accompanying drawings.

In the drawings:

FIG. 1 is a schematical view showing the syringe of this invention in longitudinal section;

FIG. 2 is a schematical view showing a variation of the syringe shown in FIG. 1, also in longitudinal section;

FIGS. 3 to 7 are respective schematical detail views of the syringe shown in FIG. 2;

FIG. 8 is a longitudinal section view showing schematically a second variation of the syringe of FIG. 1;

FIGS. 9 and 10 are respective detail views of the syringe shown in FIG. 8;

FIG. 11 is a longitudinal section view showing schematically a further variation of the syringe of FIG. 1; and FIGS. 12 to 14 are respective detail views of the syringe shown in FIG. 11.

With reference to the drawing views, generally and schematically shown at 1 is a disposable apyrogenous syringe according to the invention.

The syringe 1 comprises a syringe body 2 made of a clear synthetic plastics material and having a tubular shape open at one end and tapering at the opposite end with a bottom wall 23 formed centrally with a bore 24. Through that bore 24 there is passed and guided for sliding movement a hypodermic needle 10 which is carried on a pad 29 fitting inside the body 2.

The syringe 1 also comprises a plunger or piston 13 slidably within the body 2.

Advantageously, an engagement peg 27 is provided which has an substantially mushroom-shaped head 32 and is a unitary construction with the plunger end 28 inside the body 2; in addition, said pad 29 is formed with an engagement seat 30 for receiving said peg 27.

Mounted to the end 28 of the plunger 13 is a seal 27 which is elastically yielding in nature and has a non-uniform thickness. More specifically, it includes a portion 31 of increased thickness which defines a surface arranged to slope slightly toward the pad 29.

The syringe of this invention operates as described herein below.

After the liquid to be injected has been drawn in and the injection cycle completed, the end 28 of the plunger 13, and specifically the peg 27 thereon, is engaged with the pad 29 by applying a slight pressure on the plunger and, concurrently therewith, compressing the seal 15 elastically.

The needle is drawn manually away by moving the plunger 13 backwards to where the needle frees itself from the guide provided by the bore 24.

The thicker portion 31 of the seal 15 will exert on the pad 29 a pressure force which is directed laterally of and offset from the needle own axis on account of its higher elastic deformation. As a result, the needle 10 is brought out of alignment, thereby it cannot be re-inserted through the bore 24 and permit re-use of the syringe.

With particular reference to the example shown in FIG. 8, a variation of the inventive syringe will be now described. In this variation, cooperating items and parts which have the same construction as and operate similarly to the preceding embodiment are denoted by similar reference numerals.

In this variation, the hypodermic needle 10 is mounted to substantially form an extension of an axially hollow rod 4 which has a head 33 next to the needle provided with a seal 20. The head 33 is formed with a seat 17 for receiving an engagement peg 37 affixed centrally to the end 28 of the plunger 13.

That peg 37 is formed centrally on a member 16 connected to the end 28 via a rubber seal 15.

A safety device mounted externally of the body 2 end adjacent to the needle 10 is also provided. This device 18 is essentially a crescent-shaped shutter plate being journalled outside the bottom wall 23 of the body 2 and constantly biased by a spring 19 toward a position where it would block the bore 24 through which the needle 10 is arranged to pass.

The operation of the syringe according to this variation is substantially similar to that of the embodiment previously discussed in that the needle is withdrawn into the syringe body manually by retracting the plunger 13.

Once the rod 4 has been slipped off the guide formed by the bore 24, the shutter 18, being no longer constrained by the presence of the rod 4, will be automatically shifted to a position blocking the bore 24 by the elastic bias force from the spring 19, thereby making the syringe impossible to re-use.

It is further contemplated that the seal 15 connecting the member 16 to the end 18 has yielding properties selected to defeat any attempt at forcibly pulling the needle out of the syringe.

A second variation of the syringe according to the invention is shown in FIG. 2.

In this variation, a coil spring 3 is provided inside the body 2 which has predetermined rate and calibration.

The hypodermic needle 10 is mounted to be an extension of the axially hollow rod 4, which has its head 33 next to the needle provided with a peripherally tight-fitting seal 5. Also provided is a yielding means to hold said spring 3 in a pre-compressed state.

Above the seal 5 there is mounted a centrally bored expansible washer 6 the outside diameter whereof is slightly less than the inside diameter of the body 2.

Provided on the interior of the body 2 is a groove 14 extending radially to the syringe axis and being located at a predetermined height, indicated at X.

The spring 3 is first wound around the rod coaxially therewith and then inserted into the body 2 to lie between the bottom wall 23 and the head 33 of the rod 4. That spring is compressed until the washer 6 registers with the groove 14.

A conically shaped spreader member 7, formed in turn with a central bore 36, is inserted into the central bore 34 of the washer 6 such that the latter can fit on expanding into the groove 14 and hold the spring 3 in a pre-compressed state.

In this variation, the end 28 of the plunger 13 mounts a conventional seal 8, and provided at the open rear end of the body 2 is a plate-like stop 9 effective to prevent the plunger from slipping fully off the body 2.

In addition, a pin 35 is affixed centrally to the plunger end and effective to intercept the spreader member 7.

The reference numeral 11 denotes a safety device mounted externally of the body 2 end adjacent to the needle 10. This device is essentially a crescent-shaped shutter plate journalled on the exterior of the bottom wall 23 of the body 2 and constantly biased by a spring 12 toward a position where it blocks the bore 24 through which the needle 10 is passed.

The operation of a syringe according to this variation is described herein below, with the assumption that a liquid to be injected has been first drawn into conventionally by operation of the plunger 13.

On completion of the injection cycle, by applying a certain pressure force on the plunger 13, the pin 35 is caused to act on the member 7 and release the washer 6.

On the plunger being pushed fully down, the member 7 will be made to drop in the rod 4 and release the washer 6, which is thus restored to its original diameter.

As a result, the pre-compressed spring 3, being no longer constrained, will be allowed to expand and automatically push the rod 4 and needle 10 upwards until the latter becomes fully retracted inside the body 2.

Concurrently therewith, the shutter 11, being no longer constrained by the presence of the rod 4, will be automatically shifted to block the bore 24 by the elastic bias from the spring 12.

A further variation will be now described with reference to FIG. 11.

In this variation, a discrete means is provided for holding the spring 3 pre-compressed inside the body 2.

In particular, the needle 10 is mounted on a holding slider 21 provided peripherally with a seal 5. The spring 3 is inserted in a pre-compressed state between the bottom wall 23 of the body 2 and that slider 21. In this connection, there are provided a substantially C-shaped spring washer 26 and a small ball 25 having a larger diameter than the inside diameter of the washer 26.

The ball 25 is forced into the central portion of the washer which, on expanding, will lock securely against the inner walls of the body 2 at the height indicated at X.

Similarly to the example previously described, a pin 35 is provided on the end 28 of the plunger 13 and adapted to intercept, as the plunger is completing its stroke, the ball 25 and push it into a seat 37 formed on the slider 21 at the needle 10 inlet, thus releasing the washer 26.

For completeness of illustration, it should be noted that the bottom wall 23 of the body 2 consists of an interfitted end cap formed with the calibrated bore 24 through the center whereof the hypodermic needle 10 is made to pass.

That end cap 38 is provided for those instances where the parts making up the syringe of this invention ought to be assembled and installed with a simplified and/or more convenient procedure.

In addition, a stop 22 is provided which consists of a C-like retaining ring fitted into a groove at the open rear end of the body 2. That stop 22 is effective to prevent the plunger 13 from slipping out of the syringe body.

On the pin 35 intercepting the ball 25 and releasing the washer 26, the latter will resume its original diameter, which is somewhat less than the inside diameter of the body 2, thus allowing the pre-compressed spring 3 to expand.

This expansion movement of the spring 3 will drive the slider 21 in a guided fashion away from the bottom wall 23 of the body 2, to automatically retract the needle 10 inside the body 2 and out of the calibrated bore 24.

Once taken out of the guiding bore 24, the needle 10 will be moved out of alignment by the elastic flexibility of the rubber seal 5 which is unable to hold the needle point aligned. As a result, should an attempt be made to push the needle out by means of the plunger, it would trip on the syringe bottom and bend.

In any case, it would be impossible to re-use the syringe also because, once the spring 3 is released, the plunger end would remain at all times in contact with the slider 21 and hinder accordingly sucking in any liquids.

The syringe of this invention has a major advantage in that it comprises a peculiarly low number of component parts, and may be manufactured in large and very large volumes on the same automated assembling equipment as currently used by most manufacturers.

In addition, a syringe according to this invention does provide single use capabilities by ensuring irreversible retraction of the needle into the syringe body.

I claim:

1. A disposable safety syringe, comprising:
a syringe body;
a plunger engageable with said body for sliding movement within said body;
a hypodermic needle having an extended position outside said body and a retracted position within said body;
an engagement peg formed at one end of said plunger;
a supporting pad, for supporting said needle, arranged within said body for axial movement within said body, said pad having an engagement seat formed therein for engagement with said peg; and
an elastically yielding seal mounted to said one end of said plunger;
wherein said elastically yielding seal applies an elastic pressure to said needle when said needle is retracted into said body for biasing the needle out of alignment with the longitudinal axis of the needle when the needle is in an extended position.

2. A syringe according to claim 1, wherein said peg is provided with a substantially mushroom-shaped head.

3. A syringe according to claim 1, wherein said seal is mounted to said one end of said plunger at a location inboard relative to said peg.

4. A syringe according to claim 1, wherein a portion of said seal slopes gently away from said one end of said plunger such that said seal is provided with a nonuniform thickness.

5. A syringe according to claim 1, wherein said seal is mounted to an exterior surface of said one end of said plunger.

6. A syringe according to claim 1, wherein said peg is integrally formed with said one end of said plunger.

7. A disposable safety syringe, comprising:
an elongate syringe body;
a plunger engageable with said body for sliding movement within said body;
a hypodermic needle having an extended position outside said body and a retracted position within said body;
an engagement peg integrally formed with and extending from one end of said plunger;
a supporting pad, for supporting said needle arranged within said body for axial movement within said body, said pad having an engagement seat formed therein for engagement with said peg; and
an elastically yielding seal mounted to an exterior surface of said one end of said plunger, said seal having a portion that slopes gently away from said end of said plunger such that said seal has a nonuniform thickness;
wherein said elastically yielding seal applies an elastic pressure to said needle offset from the longitudinal axis of the syringe body for biasing the needle out of alignment with said axis when said peg engages said engagement seat and said needle is retracted into said body.

* * * * *